United States Patent [19]
Johnsen et al.

[11] Patent Number: 5,368,482
[45] Date of Patent: Nov. 29, 1994

[54] DENTAL INSTRUMENT SERVICING SYSTEM

[75] Inventors: James B. Johnsen; Hal J. Oien, both of Beaverton, Oreg.

[73] Assignee: Jordco, Inc., Beaverton, Oreg.

[21] Appl. No.: 189,919

[22] Filed: Feb. 1, 1994

[51] Int. Cl.⁵ .................. A61C 3/00; A61B 19/02; B65D 1/00

[52] U.S. Cl. .................. 433/163; 433/49; 206/63.5; 224/217

[58] Field of Search .............. 433/25, 49, 72, 75, 433/77, 163; 224/217; 206/63.5, 368; 223/106, 107, 108, 109 R

[56] References Cited

U.S. PATENT DOCUMENTS

| | | |
|---|---|---|
| 2,222,741 | 11/1940 | Bush . |
| 2,539,940 | 1/1951 | Abramson . |
| 2,665,479 | 1/1954 | Weldon ............................ 433/163 |
| 3,107,832 | 10/1963 | Kotkins ........................... 223/109 R |
| 3,327,391 | 6/1967 | Malm ............................... 433/163 |
| 3,473,991 | 10/1969 | Ludwig ........................... 223/109 R |
| 3,933,286 | 1/1976 | Karkas ......................... 223/109 R X |
| 4,280,808 | 7/1981 | Johnson et al. ................. 433/102 X |
| 4,427,130 | 1/1984 | Szigeti ............................ 221/4 |
| 4,643,674 | 2/1987 | Zdarsky .......................... 433/102 |
| 4,717,057 | 1/1988 | Porteous ....................... 433/163 X |
| 4,844,308 | 7/1989 | Porteous ......................... 224/217 |
| 4,901,847 | 2/1990 | Kesling ........................... 206/63.5 |
| 4,976,615 | 12/1990 | Kravitz ........................ 433/102 X |
| 5,016,795 | 5/1991 | Porteous ......................... 224/217 |
| 5,139,188 | 8/1992 | Scharf ............................ 224/217 |

*Primary Examiner*—Gene Mancene
*Assistant Examiner*—Nicholas D. Lucchesi
*Attorney, Agent, or Firm*—Kolisch Hartwell Dickinson McCormack & Heuser

[57] ABSTRACT

A finger-mounted dental instrument servicing system is provided which is adapted both to clean a dental instrument and to carry a medicament which may be applied thereto. The system includes socket-forming member which defines a socket to which both a cushion and medicament holder are secured. The socket-forming member also carries a finger mount by which the system is made attachable to a user's hand. The medicament holder is configured to hold a medicament such as dental paste adjacent the cushion so that an instrument may be both cleaned and charged with a dosage of medicament on a single pass.

3 Claims, 2 Drawing Sheets

DENTAL INSTRUMENT SERVICING SYSTEM

TECHNICAL FIELD

The present invention relates generally to the field of dentistry, and, more particularly, to a finger-mounted system whereby the servicing or dental instruments may be achieved. Although useful in a variety of contexts, the system is believed to be especially well suited for use in the servicing or dental cleaning and polishing instruments and is described in that context below.

BACKGROUND ART

During conventional dental maintenance and treatment procedures, dentists and dental technicians arc required to perform tasks using instruments which require periodic servicing. Such instruments are commonly used in the context of dental cleaning and polishing, a procedure which involves the removal or debris from a patient's teeth. The principle instruments employed during this procedure include a dental scraper (which is used to scrape debris from a patient's teeth) and a dental polisher (which polishes the patient's teeth using a medicament such as prophylactic paste). Both of these instruments require the periodic removal of debris which collects during use on a given patient, the dental polisher (paste applicator) further requiring the periodic application or a dosage of paste.

In the past, these servicing junctions have been accomplished with the aid of an assistant, the assistant generally being given the tedious task of holding a cloth on which the instruments may be wiped, or holding a container which carries the prophylactic paste. This arrangement, however, represents a waste of valuable time, the efforts of two professionals being used where the efforts of one professional would suffice. One alternative has been to simply place the cloth and paste on a tray where they may be accessed by the dentist or technician without the aid of an assistant. Not surprisingly, this arrangement also leads to a waste of time, the dentist or technician being required to pick up the cloth or paste each time an instrument is to be serviced. Another alternative involves the use of finger-mounted prophylactic paste holder units, but such units generally are single-purpose appliances which do nothing more than hold prophylactic paste. Known paste holders do not address the need for cleaning appliances, the dentist or technician instead being required to rely on an assistant or on the ability to place such an appliance on a nearby tray. What is needed is a more complete servicing system which may be mounted to the user's hand.

SUMMARY OF THE INVENTION

The invented dental instrument servicing system is a finger-mounted system which includes socket-forming member configured to support both a cleaning cushion and a medicament holder capable of carrying a medicament such as prophylactic paste. The socket-forming member defines a tapered socket, the cushion being similarly tapered for receipt within the socket with a portion of the cushion projecting through the socket so as to provide a wiping surface on which dental instruments may be cleaned. The medicament holder is also secured to the socket-forming member, the holder being fitted both with a clip which fastens to the socket-forming member and with a grip which holds a single-patient cup of prophylactic paste. The paste is held adjacent the cushion's wiping surface so that an instrument may be both cleaned and charged with a dosage of medicament in a single pass. A finger mount is also secured to the socket-forming member to provide for attachment of the system to a user's hand.

It is an object of this invention to provide a finger-mounted unit which is capable of cleaning dental instruments, and of carrying a medicament such as prophylactic paste. Another object of the invention is to provide a medicament holder capable of holding a medicament in a position adjacent a cushion such that an instrument may be cleaned and charged with a dosage medicament in a single pass. It is also an object of the invention to provide a multi-purpose system which can be worn on a user's hand without significantly limiting the use of that hand. These and other objects and advantages of the present invention will be more readily understood after a consideration of the drawings and the detailed description of the preferred embodiment which follows.

DETAILED DESCRIPTION OF THE PREFERRED EMBODIMENT AND BEST MODE FOR CARRYING OUT THE INVENTION

The present invention relates to a system which has been adapted for use in the servicing of dental instruments, such servicing involving the periodic removal of debris from an instrument, and the periodic charging of the instrument with a medicament such as prophylactic paste. The invention arises from the recognition of a new, more varied use of an apparatus which we previously developed, and from the adaptation of that apparatus for such varied use. The previously-developed apparatus is the subject of U.S. Pat. No. 4,280,808, which is entitled "Endodontic File Holder", and which is commonly owned herewith. The disclosure of that patent is incorporated herein by this reference.

Figure 1:
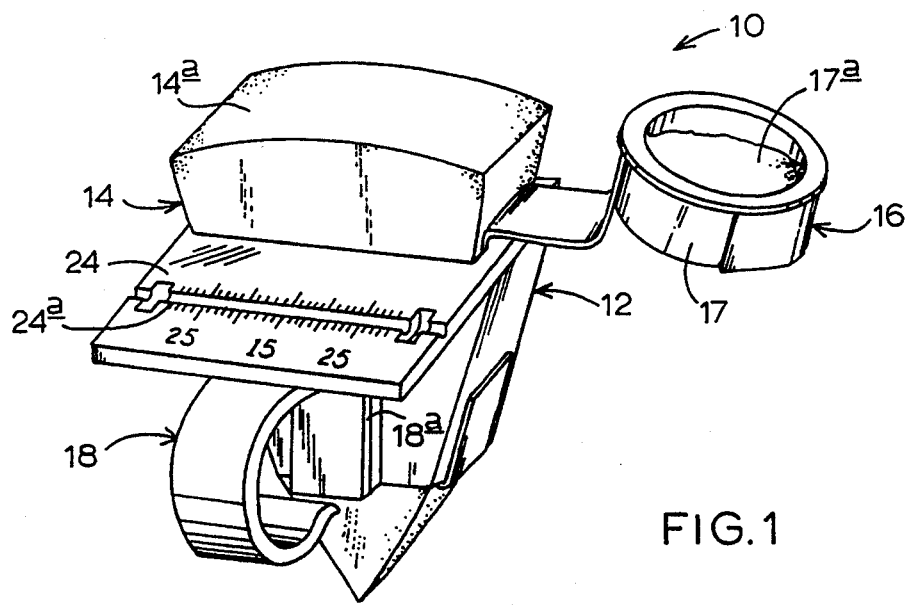
FIG. 1 is an isometric view of a preferred embodiment dental instrument servicing system, the system having been adapted to hold a conventional single-patient prophylactic paste cup.

Referring initially to FIG. 1, the reader is provided with an isometric illustration of the preferred embodiment servicing system, the system being indicated generally at 10. As shown, system 10 includes a socket-forming member 12 which in turn carries a cushion 14, a medicament holder 16, and a finger mount 18. The cushion 14 provides a cleaning surface 14a which may be used to wipe debris from a dental instrument. The medicament holder 16 is configured to receive a medicament cup 17, cup 17 generally being in the form of a package used to contain a single-patient quantity of prophylactic paste 17a. Finger mount 18 is adapted for attachment to a user's finger such that the system may be mounted on a user's hand (see FIGS. 4 and 5). It will thus be appreciated that the present system is suitable for use as a finger-mounted service station, the system being adapted to accommodate both the periodic removal of debris from an instrument and the periodic charging of the instrument with a dosage of prophylactic paste. More specific descriptions of the system's principle components are provided below.

Figure 2:
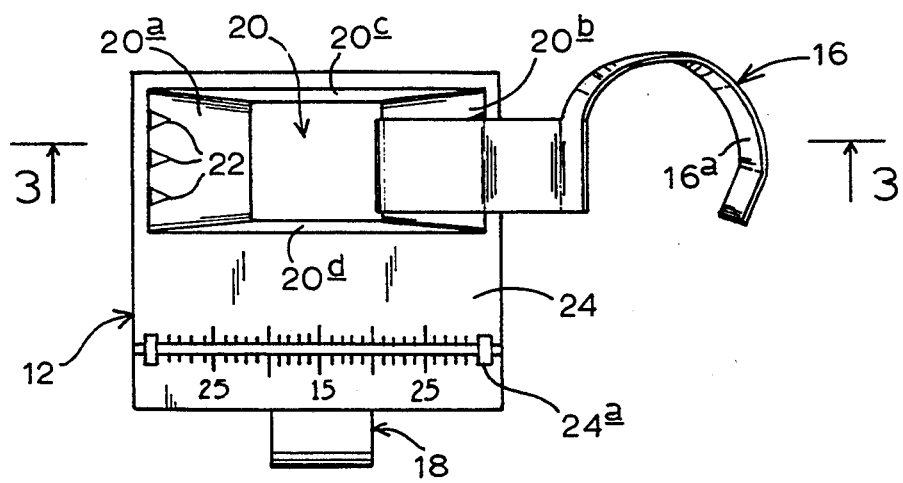
FIG. 2 is a top view of the preferred embodiment system, the system's cushion having been removed.
Figure 3:
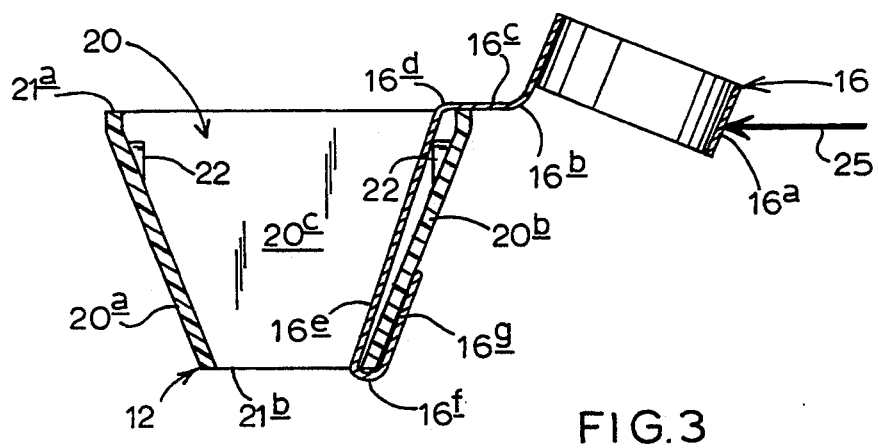
FIG. 3 is a sectional side view of the system shown in FIG. 2, the view being taken generally along line 3—3.

Focusing first on the details of the socket-forming member, and referring for that purpose to FIGS. 1-3, it will be noted that the socket-forming member defines a double-open-ended socket 20, such socket providing a seat for cushion 14. As indicated, socket-forming member 12 includes four, generally planar side walls 20a, 20b, 20c, 20d which taper between the socket-forming member's upper end 21a and lower end 21b. The walls tend toward convergence at the socket-forming member's lower end so as to define a socket which will tightly fit deformable cushion 14. In the preferred embodiment, walls 20a, 20b converge at an angle of about 40-degrees, and walls 20c, 20d converge at a much smaller angle of about 3-degrees. The socket is thins defined with an inverted, truncated, generally pyramidal shape, with the cross-sectional area of the socket decreasing continuously from its upper end to its lower end (as viewed in FIG. 3).

As illustrated in FIGS. 2 and 3, the system's side walls may be formed with projections 22, providing frictional anchors which help to maintain the cushion within the socket. In the preferred embodiment, the projections preferably are integrally molded with the side wall and are formed adjacent the socket's upper end. These projections also allow for a better fit between the socket-forming member and the medicament holder as will be described below.

In the depicted form, socket-forming member 12 also includes an outwardly projecting shelf 24, the shelf extending from wall 20d adjacent the socket-forming member's upper end so as to cover finger mount 18. Shelf 24 thus serves to protect the user's finger from injury by sharp instruments during service of such instruments by the system which is now being described. Those skilled will appreciate that the shelf may also serve as a measuring device for use in connection with endodontic files, the shelf being provided with a trough 24a and an adjacent scale. The use of such a measuring device is more fully described in the aforementioned U.S. Pat. No. 4,280,808 which has been incorporated by reference above.

Although not required, the socket-defining member is preferably of unitary construction, being formed of a lightweight material such as plastic or aluminum. These materials, it will be appreciated, are inexpensive, are formable by molding process, and are suitable for hand-worn use.

Returning to a discussion of the system's cushion, and referring for that purpose specifically to FIG. 1, it will be noted that cushion 14 is configured for insertion in socket 20, the cushion being formed of a resilient, sponge-like material suitable for use in cleaning dental instruments as will be described below. In its preferred form, the cushion is generally pie-shaped, being adapted to closely conform to the shape of the socket when placed therein. To assemble the system, the cushion is removably inserted into the socket's upper opening, the lowermost portion of the cushion being pulled through the lower opening of the socket. Because the cushion is somewhat abrasive, it provides excellent frictional adherence to the socket-forming member.

An arcuate upper wiping surface 14a provides a surface across which instruments may be passed to remove debris from the instrument. The cushion's abrasive also makes for an excellent surface against which instruments may be wiped to remove debris. Wiping surface 14a is immediately adjacent medicament cup 17, the user thus being able to both clean an instrument and charge it with a dosage of medicament during a single pass of the instrument across the system. The upper surface of the cushion is arcuate, providing a greater wiping surface area than would otherwise be provided by a flat surface. Because the cushion is replaceable with each new patient, the system is thus made adaptable for non-contaminated use with each new patient the dentist or technician serves.

Referring still to FIG. 1, it will be noted that finger mount 18 is also attached to socket-forming member 12, allowing for securement of the system to an individual's forefinger for use during a dental procedure as will be described. The finger mount is preferably removably attached to the socket-forming member via a cooperative slide arrangement 18a, the specifics of which were described in our previously issued U.S. Pat. No. 4,280,808 which has been incorporated by reference herein. Those skilled in the art will appreciate that the depicted arrangement is representative only and that a variety of different finger-mounting arrangements may similarly be used.

FIG. 1 illustrates use of the system in connection with a medicament cup 17, such cup being representative of the type of container in which single patient dosages of medicaments such as dental paste are generally packaged and sold. As indicated, cup 17 is sized to contain an amount of paste 17a suitable for use in polishing the teeth of a single patient. The cup is formed as a cylindrical container with an open mouth about which extends an outwardly disposed lateral flange. A removable cover (not shown) generally overlies the mouth of the container and is removable when the paste is to be used. Holder 16 is specifically adapted to carry such a medicament cup.

Focusing now on the specifics of holder 16, and referring specifically to FIG. 2, it will be evident that holder 16 is made up of a somewhat arcuate cup-gripping section 16a from which extends downwardly a clip section (16b through 16g). The cup-gripping section is adapted for capture of a medicament cup 17 (FIG. 1), and the clip section is adapted for attachment to the socket-forming member 12. In the depicted embodiment, cup-gripping section 16a is flattened adjacent its terminal end so as to provide for a tighter grip of the medicament cup. The clip section includes a series of bends and elongate spans, beginning with a first bend 16b which connects the holder's cup-gripping section 16a to a cup offset span 16c. The cup offset span, it will be appreciated, offsets the medicament cup from cushion 14. A second bend 16c connects cup offset span 16c to internal extension span 16e, span 16e extending along the interior of wall 20b (or, in the alternative, along wall 20c). Tension of the clip is maintained by projections 22. A third bend 16f and an exterior extension span 16g cooperate with span 16a to pinch the socket-forming member's side wall, such pinching being effective to secure the holder to the socket-forming member 12. It will thus be appreciated that the clip section extends from the cup-gripping section in a configuration which conforms to the shape of the socket-forming member, extending through the socket and clipping itself to the socket-defining member's wall. The medicament cup 17 is thus held at a level which corresponds to the arcuate upper surface 14a of cushion 14 (see FIG. 1). This allows for free flowing motion between the cushion and the medicament holder such that an instrument may be cleaned and medicament applied in a single pass.

The holder is removable from the socket-defining member (once the cushion is removed) by pushing the cup-gripping section 16a inwardly as indicated by arrow 25. By lever action, the terminal end of span 16a slides down the outer surface of wall 20b. The interior surface of span 16e is correspondingly pushed against lower end 21b and the holder is urged downwardly, pulling section 16a downwardly through the socket as viewed in FIG. 2. Holder 16 is thus removed from socket-defining member 12.

In its preferred form, the holder is formed from an aluminum sheet, the holder being cut in a L-shaped configuration and then bent to its depicted form. This arrangement allows for a system which is inexpensive to manufacture and which may be worn on a user's hand. It will be appreciated, however, that the holder may similarly be formed from a material such as plastic, and could be integrally molded with the socket-defining member. The latter arrangement, however, would detract from the ambidextrous nature of the system, the user being required to reach around the socket-defining member where the system is adapted for use on an individual's opposite hand.

Figure 4:
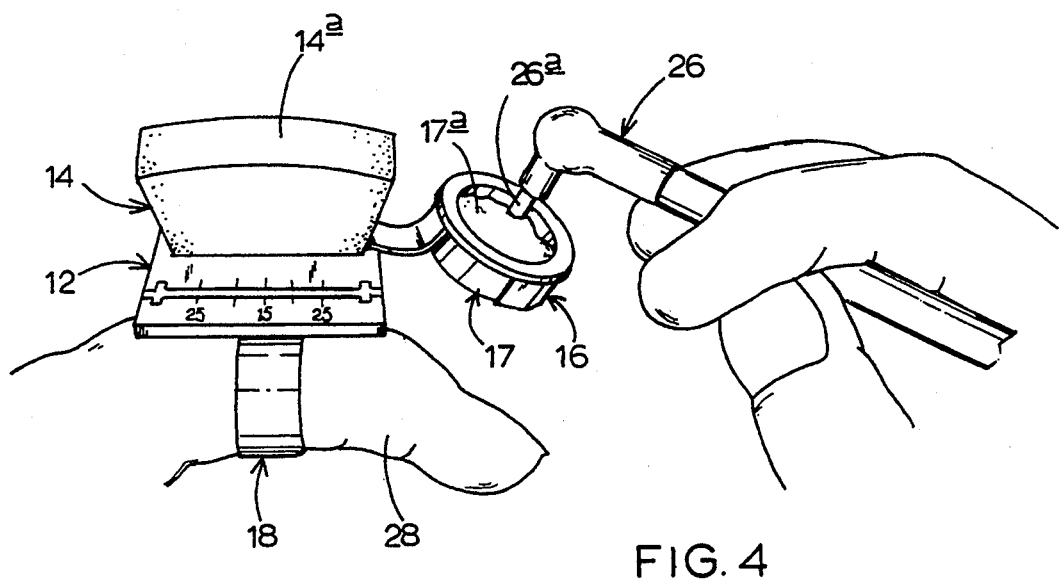
FIG. 4 is an isometric view of somewhat reduced scale, illustrating the invented system as it is used in connection with a dental paste applicator.
Figure 5:
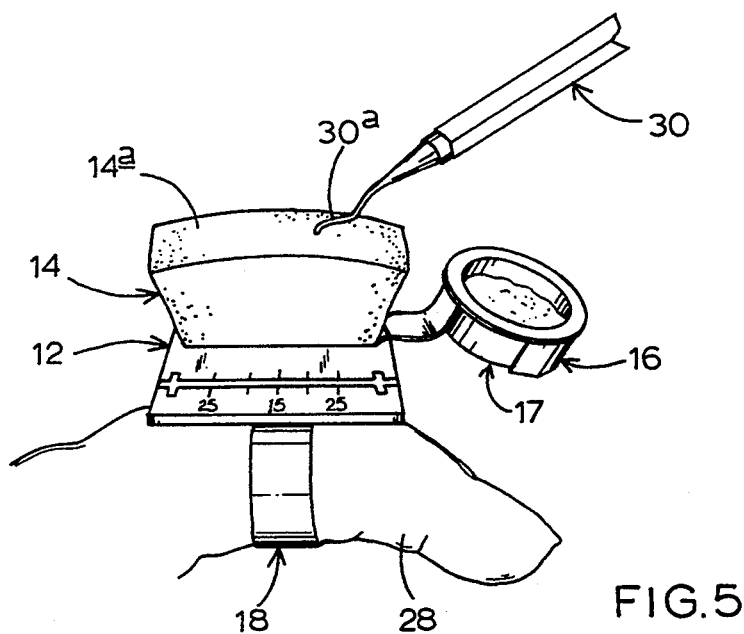
FIG. 5 is an isometric view similar to that of FIG. 4, the system being illustrated in connection with a dental scaler.

In FIGS. 4 and 5, the system is shown during its intended use, FIG. 4 illustrating use of the system in connection with a mechanized prophylactic paste applicator 26, and FIG. 5 illustrating use of the system in connection with a dental scraper 30. As indicated, the system is suited for attachment to a user's finger in either setting, finger mount 18 encircling the user's forefinger 28 and the next finger being used to stabilize the system from below (not shown). Because the system is relatively lightweight, it is not appreciatably more burdensome than a large ring, and does not significantly interfere with use of the wearer's hand.

When servicing paste applicator 26, the instrument's head 26a may be cleared of debris by wiping the head across the wiping surface 14a. The head may then be dipped into the medicament cup 17 and medicament 17a applied as shown in FIG. 4.

To service dental scraper 30, scraper tip 30a of the scraper is inserted into the cushion or brushed across the surface of the cushion, removing particulate matter or other debris from the scraper so that the scraper may again be used in the patient's mouth. An illustration of this cleaning is provided in FIG. 5.

While a preferred embodiment of the present invention has been shown and described with reference to the foregoing operational principles and preferred embodiment, it will be apparent to those skilled in the art that other changes in form and detail may be made without departing from the spirit and scope of the invention as defined in the appended claims.

We claim:

1. A dental instrument servicing system for use in cleaning a dental instrument and applying a medicament thereto, the system comprising:
   a socket-forming member;
   a resiliently deformable cushion adapted for deformed seating within said socket-forming member with a first end of said cushion extending upwardly therefrom, said first end providing a wiping surface for cleaning a dental instrument;
   a medicament holder secured to said socket-forming member, said medicament holder including a gripper configured to capture a medicament cup for maintaining a charge of medicament adjacent said cushion; and
   a finger mount joined with said socket-forming member to provide for attachment of said system to a user's hand.

2. A dental instrument servicing system for use in cleaning a dental instrument and applying a medicament thereto, the system comprising:
   a socket-forming member;
   a resiliently deformable cushion adapted for deformed seating within said socket-forming member with a first end of said cushion extending upwardly therefrom, said first end providing a wiping surface for cleaning a dental instrument;
   a medicament holder removably attachable to said socket-forming member, said medicament holder being capable of maintaining a medicament adjacent said cushion; and
   a finger mount joined with said socket-forming member to provide for attachment of said system to a user's hand.

3. A dental instrument servicing system for use in cleaning a dental instrument and applying a medicament thereto, the system comprising:
   a socket-forming member;
   a resiliently deformable cushion adapted for deformed seating within said socket-forming member with a first end of said cushion extending upwardly therefrom, said first end providing a wiping surface for cleaning a dental instrument;
   a medicament holder secured to said socket-forming member, said medicament holder including a clip with an internal span which extends through said socket and an external span which extends along an exterior of said socket said internal and external spans collectively securing said holder to said socket-forming member so as to maintain a charge of medicament adjacent said cushion; and
   a finger mount joined with said socket-forming member to provide for attachment of said system to a user's hand.

* * * * *